United States Patent [19]

Palinczar

[11] Patent Number: 4,724,139
[45] Date of Patent: Feb. 9, 1988

[54] ANTIPERSPIRANT STICK

[76] Inventor: Victor Palinczar, 435 Adeline St., Trenton, N.J. 08611

[21] Appl. No.: 731,871

[22] Filed: May 8, 1985

[51] Int. Cl.⁴ .......................... A61K 7/34; A61K 7/38
[52] U.S. Cl. ............................... 424/66; 424/DIG. 5; 424/68
[58] Field of Search ....................... 424/DIG. 5, 66, 68

[56] References Cited

U.S. PATENT DOCUMENTS

| Re. 29,871 | 12/1978 | Papantoniore et al. | 424/DIG. 5 |
|---|---|---|---|
| 1,869,782 | 8/1932 | Sternberg et al. | 424/DIG. 5 |
| 3,957,969 | 5/1976 | Fujiyama et al. | 424/DIG. 5 |
| 4,049,792 | 9/1977 | Elsnau | 424/DIG. 5 |
| 4,137,306 | 1/1979 | Rubino et al. | 424/DIG. 5 |
| 4,229,432 | 10/1980 | Geria | 424/DIG. 5 |
| 4,346,079 | 8/1982 | Roehl | 424/DIG. 5 |
| 4,393,044 | 7/1983 | Takada et al. | 424/DIG. 5 |

FOREIGN PATENT DOCUMENTS 2852988  6/1979  Fed. Rep. of Germany ... 424/DIG. 5

*Primary Examiner*—Dale R. Ore
*Attorney, Agent, or Firm*—Sachs & Sachs

[57] ABSTRACT

A highly effective antiperspirant composition being essentially water-insoluble with the exception of the active astringent antiperspirant particles formed as a stick includes from about 5% to about 80% of a volatile isoparaffin liquid carrier, from about 5% to about 60% of one or more water-insoluble waxes and from about 8% to about 60% of an active aluminum or zirconium astringent antiperspirant salt in the form of finely divided particles.

15 Claims, No Drawings

ANTIPERSPIRANT STICK

BACKGROUND OF THE INVENTION

1. Field of the Invention

This invention relates to very effective and novel antiperspirant compositions in an acceptable cosmetic base. More specifically, this invention relates to essentially anhydrous antiperspirants in the form of solid sticks which have the ability to maintain their physical structure over a long time and still produce an elegant feel when applied to the skin without any adversities, e.g. tack or drag; the skin is left feeling smooth and soft while retaining antiperspirant activity.

2. Discussion of the Relevant Art

Numerous stick antiperspirant compositions are known, and have been published in a variety of cosmetic journals and by suppliers of cosmetic ingredients. Those skilled in the art have accepted the fact that anhydrous antiperspirant stick systems are more advantageous to market and have good consumer acceptance primarily due to the ease of application to the skin, good cosmetic aesthetics and an acceptable degree of effectiveness. Previous to the development of anhydrous stick systems numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin and their consistency and effectiveness are questionable.

Antiperspirant stick systems consisting of low molecular weight monohydric alcohols in conjunction with polyhydric alcohols as described in U.S. Pat. No. 4,137,306, issued to Rubino, have the advantage of quicker drying rates, but the residue of the polyhydric alcohols in combination with the atringent salts produces a high degree of tack and their effectiveness is limited to the type and amount of astringent salts that could be incorporated therein. It should be noted that sticks of this nature have never been successfully marketed.

Anhydrous stick compositions that suspend the aluminum salt in a hydrophobic matrix as described in U.S. Pat. No. 4,049,792, issued to Elsnau, make use of waxy materials and a long chain of fatty esters to form a stick that delivers the active astringent salts to the skin. Preparations made by these teachings are rather greasy and they envelop the active astringent salt for long periods of time preventing their maximum performance. To alleviate this inherent negative characteristic volatile silicone fluids replaced the lesser volatile long chain fatty esters as described by U.S. Pat. No. 4,126,679, issued to Davy et al. Davy teaches the advantage of incorporating a volatile, non-staining liquid such as cyclic dimethylpolysiloxanes, referred to as volatile silicones, as a carrier in combination with various types of waxes for the active astringent salts in an antiperspirant stick composition. Similar antiperspirant stick compositions containing volatile silicones are described by U.S. Pat. Nos. 4,151,272, 4,280,994 and 4,435,382.

Although the volatile silicone based antiperspirant stick compositions are effective and highly aesthetic they may contain up to 80% by weight of volatile silicone. The use of such large amounts of volatile silicone make preparations prepared very expensive. Attempts to decrease or replace the volatile silicone content in anhydrous antiperspirant stick composition to reduce cost is constant and is exemplified in U.S. Pat. Nos. 4,425,328 and 4,229,432. These types of compositions, however, are more oily with longer dry out rates and are less appealing to the consumer.

In order to overcome the shortcoming of known anhydrous antiperspirant sticks the present invention replaces the volatile silicone with non-polar volatile liquid ingredients, in part or in total. There is a need for such a replacement to lower the cost of producing antiperspirant sticks while still giving the consumer an effective highly aesthetic product. Inexpensive ingredients, having the same desirable attributes of volatile silicone, namely, low irritation, low degree of fabric staining, good volatility, compatibility with an array of non-polar organic compounds while providing good feel to the skin, is not available in anhydrous antiperspirant compositions that allow for effective and safe products. Ingredients may be available which exhibit one or more of these desired attributes but the combination of these attributes, for use in preparing anhydrous antiperspirant systems, has not been demonstrated. Ingredients fulfilling these requirements, which have not been used previous to this invention, in any anhydrous antiperspirant composition of any form are volatile isoparaffin liquids.

SUMMARY OF INVENTION

This invention relates to a very effective, highly aesthetic, low cost antiperspirant stick composition comprising volatile isoparaffin liquids in an amount up to about 80% by weight, from about 5% to about 60% by weight of water-insoluble waxes having a melting point range from about 40 degrees C. to about 100 degrees C. and from about 8% to about 60% by weight of active astringent antiperspirant salts which are relatively soluble in water in the form of finely divided particles that are homogeneously dispersed throughout the matrix of said composition.

The compositions may optionally contain from about 0% to about 65% by weight of water-insoluble emollients having a melting point less than about 22 degrees C. which are liquid at room temperature; from about 0% to about 12% by weight of water-insoluble inert filler material in the form of finely divided particles dispersed throughout the matrix of the composition; from about 0% to about 5% by weight of surface active agents; from about 0% to about 3% by weight of bactericidal agents and from about 0% to about 3% by weight of fragrance oil.

DETAILED DESCRIPTION OF INVENTION

It has been discovered that highly effective, non-irritating, cosmetically aesthetic anhydrous antiperspirant sticks containing volatile isopraffin liquids, waxes and active astringent antiperspirant salts such as aluminum, zirconium or zinc salts, are prepared by heating the isoparaffins to a temperature sufficient to solubilize the wax, and fluid enough to homogenously disperse the active astringent antiperspirant salts. Upon completion of the addition of the astringent salts, the composition is cooled and placed in the proper dispenser for consumer use.

It has also been discovered that the composition may contain numerous types of water insoluble liquid emollients for the purpose of adjusting the physical parameters of the stick relevant to texture, rigidity and product dosage. It has further been discovered that the composition may contain inert fillers to decrease the oily feel on the skin contributed by many of the ingredients used in these compositions and also to aid in strengthening the matrix of the stick composition.

It has still further been discovered that the composition may contain surface active agents, bactericidal agents, and fragrance oil. These ingredients are more specifically described below.

While applicant does not wish to be limited by any theory of the mechanism of activity of the invention, it is believed that the use of volatile isoparaffin liquids is very important in determining both antiperspirant activity and the cosmetic aesthetics of the stick antiperspirant. When antiperspirant stick composition is placed on the skin the transfer feels smooth and slippery with a dry feel. The volatile isoparaffin liquids, which are usually a major constituent of the composition, evaporate from the skin leaving a water-insoluble flexible film consisting of a high ratio of astringent salts to organic and inert ingredients. The ingredients consisting primarily of water-insoluble waxes which hold the water-soluble active astringent ingredients to the skin. The water-insoluble film helps prevent the loss of the active astringent salts by physical abrasion and the spontaneous dissolution of the active astrigent salts during initial secretion of perspiration after the antiperspirant composition is applied to the skin. Since anhydrous antiperspirant systems are activated by perspiration, the initial amount of sweat produced before any activity occurs could be sufficient to consume a major portion of the active astringent salts thereby producing a high degree of efficacy for only a short time. It is believed that the astringent salts are partially encapsulated throughout the water-insoluble film. Perspiration migrates through the film matrix by capillary action and the active astringent salts are activated in a sustained controlled manner. The film's water-insolubility prevents it from being washed away during the initial secretion of large amounts of perspiration. It is therefore believed that the combination of these actions cause these compositions to be effective for long periods of time.

VOLATILE ISOPARAFFIN LIQUIDS

Isoparaffin liquids, such as the ISOPARS manufactured by (EXXON INC., Houston, Tex.) are branched-chained (i.e., non-linear) hydrocarbons having an average molecular weight from about 100 to about 200, a boiling point of about 105 degrees to about 320 degrees C., a specific gravity of about 0.800 or less at 15.6 degrees C. a viscosity of 8 centistokes or less at 25 degrees C. and a water solubility of less than 0.0015% at 25 degrees C.

Preferred volatile isoparaffins used in this invention have a molecular weight from about 160 to about 180 and a boiling point range from about 180 degrees C. to about 200 degrees C. The present composition may contain up to 80% of volatile isoparaffin liquids. The preferred amount of volatile isoparaffin liquid is from about 30% to about 65% and most preferably from about 40% to about 55%. Amounts of less than 30% are also acceptable if used in combination with water-insoluble liquid emollients or waxes having melting points in the range from about 40 degrees C. to about 45 degrees C. Compositions containing levels of 5% by weight of volatile isoparaffin liquids having an average molecular weight from 100 to about 150 and a boiling point point range from about 150 degrees C. to about 160 degrees C. when used in combination with low molecular weight liquid emollients, such as di-isopropyl esters of dicarboxylic acids, provide adequate application to the skin with acceptable drying time and overall aesthetics.

It will be understood that if one replaces any portion of the volatile isoparaffin liquid, with one ingredient or a mixture of any ingredients mentioned in this invention that do not have rates of evaporation and viscosity similar to that of the volatile isoparaffins, compositions prepared with these ingredients or a mixture of these ingredients, will have their drying rates, antiperspirant efficacy and overall cosmetic aesthetics reduced. However, so long as the final compositions have at least 5% volatile isoparaffins by weight, these compositions will still be more appealing and effective than compositions without the use of the volatile isoparaffin liquids. It will be further understood that the volatile isoparaffin liquids provide excellent compatibility with an array of cosmetically acceptable ingredients, and any ingredient combination may be made without departing from this spirit and scope of this invention.

THE WATER-INSOLUBLE WAX

Waxes used in the present compositions are usually referred to as substances that are plastic solids at ambient temperature and, on being subjected to moderate elevated temperatures, become low viscosity liquids. Because they are plastic, waxes usually deform under pressure without application of heat. The chemical composition of waxes is complex and usually contain a broad spectrum of molecular weight species and reactive functional groups. For this reason applicant wishes not to be limited only to the waxes mentioned in the present invention.

Waxes selected from a group having a melting range between about 40 degrees C. to about 100 degrees C., a water-insolubility of less than 1% at 25 degrees C. and a dielectric constant not greater than 20 are hereinafter referred to as the water-insoluble wax of this composition. The water-insoluble wax provides the basic structure of the stick composition and enables the active astringent salts to remain on the skin. Examples of suitable water-insoluble waxes are those obtained from natural sources, such as insects and animal, e.g. beeswax and spermaceti; waxes from vegetable sources, e.g. candelilla, carnauba, Japan, Rice Bran, hydrogenated Jojoba oil, hydrogenated castor oil and bayberry wax; and waxes from mineral sources, e.g. montan, peat, ozokerite, cersin, paraffin, semimicrocrystalline and microcrystalline.

The present compositions may also contain waxes from fatty acids, e.g. elaidic, palmitic, stearic and 9,10-dihydroxyoctadelanoic; compounds of fatty alcohols, e.g. cetyl, stearyl, ceryl, and myricyl; compounds of esters, e.g. cetyl palmitate, glyceryl stearate and cetyl 2-hydroxpalmitate; and compounds of silicones, e.g. stearoxy dimethicone and hexadecyl methicone. The preferred waxes are beeswax, spermaceti, stearic acid, hydrogenated castor oil, stearyl alcohol, and glyceryl stearate. The present invention may contain from about 5% to about 60% by weight of these water-insoluble waxes or a mixture thereof. The preferred amount of water-insoluble waxes is from about 10% to about 45% by weight, most preferably from about 12% to about 30% by weight.

THE ASTRINGENT ANTIPERSPIRANT SALT

Ingredients that produce a reduction in sweat in the axilla area by physiological action are hereinafter referred to as active astringent antiperspirant salts. Examples of these astringent salts in the form of impalpable particles are aluminum chloride, aluminum chlorohydrates, aluminum sulfocarbolate, aluminum sulfate, aluminum-zirconium chlorohydrates, aluminum-zirconium tetrachlorohydrex gly., zinc sulfate, zinc sulfocarbolate, and zirconium chlorohydrate. The preferred astringent antiperspirant salts are the aluminum chlorohydrates and aluminum-zirconium chlorohydrates having a particle size from about 1 micron to about 75 microns, and preferably, from about 4 to about 25 microns. Examples of the preferred astringent antiperspirant salts are commercially available as WICKENOL CPS 331 and WICKENOL CPS 370 manufactured by Wicken, Inc., of Huguenot, N.Y., which are fine particles of aluminum chlorohydrate and aluminum-zirconium chlorohydrate respectively, having an average particle size of about 10 microns.

The present composition may contain from about 8% to about 60% of astringent antiperspirant salts suspended and homogeneously dispersed throughout the stick matrix, the preferred amount of astringent antiperspirant salts is from about 20% to about 50%, by weight, most preferable from about 25% to about 45%.

THE WATER-INSOLUBLE LIQUID EMOLLIENT

The present composition may also contain, as an optional ingredient, from about 0% to about 65% by weight of a water-insoluble liquid material. Such liquids are in the liquid state at room temperature (about 22 degrees C.) and have a water solubility of less than about 1% at 25 degrees C. From these liquids a group of liquids have been selected which are organic in nature having a low degree of irritation and toxicity, that are generally considered safe for topical use, that provide a softening or soothing effect on surface skin tissue are hereinafter referred to as the water-insoluble liquid emollients in the present composition. Preferred water-insoluble liquid emollients include fatty acids such as oleic and recinoleic; fatty alcohols such as oleyl, lauryl, and hexadecyl (ENJAY); esters such as diisopropyl adipate, benzoic acid esters of $C_9$-$C_{15}$ alcohols, and iso-nonyl iso-nonanoate; alkanes such as mineral oil; silicones such as dimethyl polysiloxane; and cyclic dimethyl polysiloxane and ethers such as polyoxypropylene butyl ethers and polyoxypropylene cetyl ethers. The most preferred water-insoluble liquid emollients are: diisopropyl adipate, 2-ethylhexyl palmitate, dimethylpolysiloxane 50 cst. and polyoxypropylene (14) butyl ether. The preferred amount of water-insoluble liquid emollient is from about 5% to about 40% by weight, preferably from about 10% to about 30%.

The water-insoluble liquid emollient can be used as an adjunct to the water-insoluble waxes to provide emolliency and also to control the rate or product depositing on the skin. One skilled in the art will easily be able to adjust the cosmetic aesthetics and physical structure by combining various suitable water-insoluble waxes and water-insoluble liquid emollients.

INERT FILLER

In addition to the ingredients named hereinbefore, it is also optional to have in the compositions from about 0% to about 12% by weight of inert particulate filler materials which do not decompose during the preparation of the stock. For example, talc, fumed silica, starch and clays may be used. All of the foregoing material are inert with the ingredients useful in the composition and may be used as an adjunct with these ingredients to increase the cosmetic aesthetics and functionality of the product and to improve the structure of the stick.

SURFACE ACTIVE AGENT

In addition to the above ingredients named hereinbefore, it is further optional to have in the composition from about 0% to about 5% by weight of surface active agents such as polyoxyethylene (25) stearyl alcohol, to facilitate removal of the composition during bathing. A number of other surface active agents suitable for this purpose are known in the art. Preferred surface active agents are selected from a group of non-ionic ethers and esters having HLB greater than 10 such as: polyoxyethylene (25) stearyl ether, polyoxyethylene (150) dioleate, polyoxyethylene (40) octyl phenyl ether and polyoxyethylene (20) sorbitan tristearate.

In addition to the above ingredients, it is desirable to include a fragrance oil, antibacterial agents, coloring agents, antioxidizing agents, pigments, etc. in small amounts. Examples of additional ingredients include oil soluble dyes, $Fe_2O_3$ (pigment), and 2,4,4'-trichloro-2'-hydroxydiphenyl ether (antibacterial agent).

The stick antiperspirant compositions of the present invention may be made a variety of ways known to those skilled in the art. In one procedure, the liquid isoparaffins and water insoluble waxes are heated to a temperature sufficient to solubilize the wax in a suitable container with agitation. When dissolution is complete, the active astringent antiperspirant salt is mixed and dispersed in the liquid isoparaffin water-insoluble wax solution. The optional ingredient may then be added or the mixture may be allowed to cool to a temperature above the solidification point before adding additional ingredients. The ingredients are mixed together to form a homogeneous suspension, cooled to a temperature sufficient to maintain fluidity while still allowing the dispersed particles to be suspended and is then poured into suitable containers.

Another procedure for preparing stick antiperspirants compositions of the present invention that employ optional ingredients such as water-insoluble liquid emollients and surface active agents, would be to heat the isoparaffin liquids, the water-insoluble liquid emollients, the surface active agent, and the water-insoluble waxes to a temperature sufficient to form a solution of these materials, followed by the addition of the active astringent antiperspirant salts with gentle agitation. Following addition of the salts, other optional ingredients such as talc may then be added and mixed until a homogenous suspension is formed. The suspension is cooled to a temperature above the solidification point and is then poured into suitable containers.

The following examples are give to further illustrate the present invention. It is to be understood, however, that the invention is not limited thereto.

EXAMPLE 1

| Ingredient | Percent by weight |
| --- | --- |
| Stearyl Alcohol | 10.0 |
| Hydrogenated Castor Oil-mp 86 degrees C. | 4.0 |

| Ingredient | Percent by weight |
|---|---|
| Aluminum Chlorohydroxide | 40.0 |
| *Isopar "V" | 45.0 |
| Fragrance | 1.0 |
| | 100.0 |

*(Isopar "V" Avg. Mol. Wt. 197 B.P. Range, 255–301 degrees C.)

EXAMPLE 2

| Ingredient | Percent by weight |
|---|---|
| Stearic Acid | 10.0 |
| Hydrogenated Castor Oil-mp 86 degrees C. | 4.0 |
| Zirconium Chlorohydroxide | 25.0 |
| Talc | 10.0 |
| *Isopar "M" | 45.0 |
| Diisopropyl Adipate | 5.0 |
| Fragrance | 1.0 |
| | 100.0 |

*(Isopar "M", Avg. Mol. Wt. 191 B.P. Range, 207–260 degrees C.)

EXAMPLE 3

| Ingredient | Percent by weight |
|---|---|
| Stearyl Alcohol | 10.0 |
| Hydrogenated Castor Oil-mp 86 degrees C. | 4.0 |
| Aluminum/Zirconium Chlorohydroxide | 30.0 |
| Distarch Phosphate | 10.0 |
| *Isopar "L" | 45.0 |
| Fragrance | 1.0 |
| | 100.0 |

*(Isopar "L", Avg. Mol. Wt. 171 B.P. Range, 188–206 degrees C.)

EXAMPLE 4

| Ingredient | Percent by weight |
|---|---|
| Hydrogenated Castor Oil-mp 80 degrees C. | 14.0 |
| Aluminum Chlorohydroxide | 30.0 |
| Isopar "E" | 40.0 |
| Talc | 10.0 |
| Mineral Oil 75 cst. | 2.0 |
| Oleyl Alcohol | 3.0 |
| Fragrance | 1.0 |
| | 100.0 |

*(Isopar "E", Avg. Mol. Wt. 120 B.P. Range, 110–150 degrees C.)

EXAMPLE 5

| Ingredient | Percent by weight |
|---|---|
| Cetyl Alcohol | 9.0 |
| Carnauba Wax | 5.0 |
| Beeswax | 2.0 |
| Aluminum Chlorohydroxide | 30.0 |
| Talc | 10.0 |
| Isopar "L" | 43.0 |
| Fragrance | 1.0 |
| | 100.0 |

EXAMPLE 6

| Ingredient | Percent by weight |
|---|---|
| Stearyl Alcohol | 10.0 |
| Hydrogenated Castor Oil-mp 86 degrees C. | 4.0 |
| Aluminum/Zirconium Chlorohydroxide | 30.0 |
| Glycine Complex | |
| Talc | 10.0 |
| Polyoxypropylene (14) Butyl Ether | 5.0 |
| Isopar "L" | 40.0 |
| Fragrance | 1.0 |
| | 100.0 |

EXAMPLE 7

| Ingredient | Percent by weight |
|---|---|
| Glyceryl Stearate | 9.0 |
| Stearoxy Dimethicone | 1.0 |
| Hydrogenated Castor Oil-mp 86 degrees C. | 4.0 |
| Aluminum Chlorohydroxide | 30.0 |
| Talc | 10.0 |
| Isopar "L" | 35.0 |
| Isopar "V" | 10.0 |
| Fragrance | 1.0 |
| | 100.0 |

EXAMPLE 8

| Ingredient | Percent by weight |
|---|---|
| Spermaceti | 10.0 |
| Paraffin Wax-mp 96–98 degrees C. | 5.0 |
| Aluminum Chlorohydroxide | 30.0 |
| Talc | 10.0 |
| Isopar "L" | 33.0 |
| Isopar "V" | 10.0 |
| Oleic Acid | 1.0 |
| Fragrance | 1.0 |
| | 100.0 |

EXAMPLE 9

| Ingredient | Percent by weight |
|---|---|
| Stearyl Alcohol | 10.0 |
| Hydrogenated Castor Oil-mp 86 degrees C. | 4.0 |
| Aluminum Chlorohydroxide | 30.0 |
| Talc | 10.0 |
| Isopar "E" | 10.0 |
| Isopar "L" | 23.0 |
| Isopar "V" | 10.0 |
| Poloxyethylene (25) Stearyl Ether | 2.0 |
| Fragrance | 1.0 |
| | 100.0 |

EXAMPLE 10

| Ingredient | Percent by weight |
|---|---|
| Stearyl Alcohol | 10.0 |
| Hydrogenated Castor Oil-mp 86 degrees C. | 4.0 |
| Aluminum Chlorohydroxide | 30.0 |
| Talc | 10.0 |
| Titanium Dioxide | 0.5 |
| Isopar "E" | 23.0 |
| Isopar "V" | 23.0 |
| Dimethylpolysiloxane 50 cst. | 1.5 |
| | 100.0 |

What I claim is:

1. In antiperspirant stick composition consisting essentially of, based on the total weight of the composition:

A. From about 5% to about 60% by weight of one or more water-insoluble waxes;

B. from about 0% to about 65% by weight of a water insoluble liquid, organic emollient compound C. from about 8% to about 60% by weight of water-soluble astringent antiperspirant salts;

D. from about 0% to about 5% by weight of a non-ionic surface active agent;

E. from about 0% to about 12% by weight of an inert particulate filler material wherein the improvement comprises:

F. from about 5% to about 80% by weight of a volatile branched-chain isoparaffin liquid carrier; having an average molecular weight from about 100 to about 200, a boiling point of about 105 degrees to about 320 degrees C., a specific gravity of about 0.800 or less at 15.6 degrees C., a viscosity of 8 centistokes or less at 25 degrees C., and a water solubility of less than 0.0015% at 25 degrees C.

2. An antiperspirant stick composition according to claim 1 wherein
said volatile, branched-chain, isoparaffin liquid carrier is present in an amount of from about 35% to about 65% and has an average molecular weight of about 160 to about 180 and a boiling range from 180 degrees C. and about 200 degrees C., a specific gravity of 0.800 or less at 15.6 degrees C., a viscosity of 8 centistokes or less at 25 degrees C., and a water solubility of 0.0015% or less at 25 degrees C.; wherein said water-insoluble waxes are present in an amount of about 10% to about 40% and are selected from a group consisting of beeswax, candelilla, carnauba, Japan, rice bran, hydrogenated jojoba oil, hydrogenated castor oil, bayberry, montan, peat, ozokerite, ceresin, paraffin, semi-microocrystalline, micro-crystalline, elaidic acid, palmitic acid, stearic acid, cetyl alcohol, stearyl alcohol, cetyl palmitate, glyceryl stearate, stearoxy dimethicone, hexadecyl methicone, myristyl alcohol and isostearic acid; and wherein said astringent antiperspirant salts are present in an amount of about 20% to about 50%.

3. An antiperspirant stick composition according to claim 1 wherein said astringent antiperspirant salts are selected from a group consisting of aluminum chlorhydroxide, aluminum sulfate, mixtures of aluminum chlorhydroxide and aluminum chloride, zirconium chlorhydroxide and complexes formed from zirconium chlorhydroxide, aluminum chlorhydroxide and glycine.

4. An antiperspirant stick composition according to claim 1 wherein:
(B) said water insoluble liquid, organic emollient compound having a water-solubility of less than about 1% at 25 degrees C. and a melting point less than 22 degrees C. is selected from the group consisting of fatty alcohols, fatty acids, esters, ethers, alkanes, and polysiloxanes and,
(E) said inert particulate filler material selected from the group consisting of talc, colloidal silica, starch, clays and clay complexes.

5. An antiperspirant stick composition according to claim 4 wherein:
(A) said water-insoluble wax is selected from the group consisting of beeswax, candelilla, carnauba, japan, rice bran, hydrogenated jojoba oil, hydrogenated castor oil, bayberry, montan, peat, ozokerite, ceresin, paraffin, semimicrocrystalline, micro-crystallines, elaidic acid, stearic acid, cetyl alcohol, stearyl alcohol, cetyl palmitate, glyceryl stearate, stearoxy dimethicone, hexadecyl methicone, myristyl alcohol, and isostearic acid;

(B) said emollient is selected from the group consisting of oleic acid, lauryl alcohol, diisopropyl adipate, mineral oil, dimethylpolysiloxane, cyclic dimethylpolysiloxane, polyoxypropylene butyl ether and isopropyl myristate;

(C) said antiperspirant salt is selected from the group consisting of aluminum chlrohydroxide, aluminum sulfate, mixtures of aluminum chlorhydroxide and aluminum chloride, zirconium chlorohydroxide, and complexes formed from zirconium chlorohydroxide, aluminum chlorhydroxide and glycine; and (D) said surface active agent is selected from the group consisting of polyoxyethylene (25) stearyl ether, polyoxyethylene (150) dioleate, polyoxyethylene (40) octyl phenyl ether and polyoxyethylene (20) sorbitan tristearate.

6. An antiperspirant stick composition according to claim 1 wherein
A. from about 10% to about 35% of one or more water-insoluble waxes having a melting point range from about 40 degrees C. to about 100 degrees C., water-solubility of less than about 1% at 25 degrees C., and average molecular weight of about 170 to about 950, a specific gravity from about 0.750 to about 1.100 at 15.6 degrees C., and a dielectric constant less than 20 at 25 degrees C. selected from the group consisting of beeswax, candelilla, carnauba, Japan, rice bran, hydrogenated jojoba oil, hydrogenated castor oil, bayberry, montan, peat, ozokerite, ceresin, paraffin, semimicrocrystalline, microcrystalline, elaidic acid, palmitic acid, stearic acid, cetyl alcohol, stearyl alcohol, cetyl palmitate, glyceryl stearate, stearoxy dimethicone, hexadecyl methicone, myristyl alcohol, and isostearic acid;

B. from about 5% to about 20% by weight of a liquid emollient selected from the group consisting of oleic acid, lauryl alcohol, diisopropyl adipate, mineral oil, dimethylpolysiloxane, cyclic dimethylpolysiloxane, polyoxypropylene (14) butyl ether and isopropyl myristate;

C. from about 20% to about 40% by weight of a water-soluble astringent antiperspirant active salt selected from the group consisting of aluminum chlorhydroxide, aluminum sulfate, mixtures of aluminum chlorhydroxide and aluminum chloride, zirconium chlorhydroxide and complexes formed from zirconium chlorhydroxide, aluminum chlorhydroxide and glycine;

D. from about 0.5% to about 3% by weight of a non-ionic surfactant selected from the group consisting of polyoxyethylene (25) stearyl ether, polyoxyethylene (150) dioleate, polyoxyethylene (40) octylphenyl ether and polyoxyethylene (20) sorbitan tristearate E. from about 4% to about 10% by weight of an inert powdered filler material selected from the group consisting of talc, colloidal silica, starch, clays and clay complexes wherein the improvement comprises:

F. from about 35% to about 65% of a volatile branched-chain isoparaffin liqid carrier; having an average molecular weight from about 100 to about 200, a boiling point of about 105 degrees to about 320 degrees C., a specific gravity of about 0.800 or less at 15.6 degrees C., a viscosity of 8 centistokes or less at 25 degrees C., and a water solubility of 0.0015% or less at 25 degrees C.

7. An antiperspirant stick composition according to claim 6 wherein the astringent antiperspirant active salt is aluminum chlorhydroxide.

8. An antiperspirant stick composition according to claim 6 wherein the astringent antiperspirant active salt is a complex formed from zirconium chlorhydroxide, aluminum chlorydroxide and glycine.

9. An antiperspirant stick composition according to claim 6 wherein the water-insoluble wax is stearyl alcohol.

10. An antiperspirant stick composition according to claim 6 wherein the water-insoluble wax is hydrogenated castor oil.

11. An antiperspirant stick composition according to claim 6 wherein the emollient is diisopropyl adipate.

12. An antiperspirant stick composition according to claim 6 wherein the emollient is dimethylpolysiloxane.

13. An antiperspirant stick composition according to claim 6 wherein the emollient is polyoxypropylene (14) butyl ether.

14. An antiperspirant stick composition according to claim 6 wherein the inert powdered filler material is talc.

15. An antiperspirant stick composition according to claim 6 wherein the non-ionic surfactant is polyoxyethylene (25) stearyl ether.

* * * * *